United States Patent [19]

Lee

[11] Patent Number: 5,089,485

[45] Date of Patent: Feb. 18, 1992

[54] ANTI-INFLAMMATORY FURANONES

[75] Inventor: Gary C. M. Lee, Laguna Hille, Calif.

[73] Assignee: Allergan, Inc., Irvine, Calif.

[21] Appl. No.: 426,243

[22] Filed: Oct. 25, 1989

Related U.S. Application Data

[63] Continuation-in-part of Ser. No. 273,294, Nov. 18, 1988, abandoned.

[51] Int. Cl.$^5$ ............... A61K 31/665; A61K 31/365; C07F 9/655; C07D 307/60
[52] U.S. Cl. ........................ 514/99; 514/63; 514/471; 514/473; 549/214; 549/222; 549/313; 549/318; 562/840
[58] Field of Search ............... 549/214, 222, 313, 318; 514/63, 99, 471, 473

[56] References Cited

U.S. PATENT DOCUMENTS

| | | | |
|---|---|---|---|
| 2,359,096 | 9/1944 | Elderfield | 260/239.5 |
| 2,359,208 | 9/1944 | Elderfield | 260/344 |
| 4,447,445 | 5/1984 | Jacobs et al. | 514/473 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |
| 4,957,917 | 9/1990 | Lee | 514/231.5 |
| 5,013,850 | 5/1991 | Lee | 549/222 |
| 5,037,811 | 8/1991 | Lee | 549/222 |
| 5,043,457 | 8/1991 | Lee | 549/222 |
| 5,045,564 | 9/1991 | Lee | 549/222 |

FOREIGN PATENT DOCUMENTS

| | | |
|---|---|---|
| 133376 | 2/1985 | European Pat. Off. |
| 209274 | 1/1987 | European Pat. Off. |
| 295056 | 6/1987 | European Pat. Off. |
| 5019 | 8/1987 | World Int. Prop. O. |

OTHER PUBLICATIONS

Bennett et al., *Molecular Pharmacology* 32 p. 587 (1987).
Bonjouklian, et al., Chemical Abstracts, vol. 106, 156260c, p. 670 (1987).
Reynolds, et al., J. Am. Chem. Soc., 110, pp. 5172-5177 (1988).
Tocanne et al., Chemical Abstracts 69 76581k, p. 7146 (1968).
Deems, et al. Biochimica et Biophysica Acta, 917 pp. 258-268 (1987).
E. D. de Silva et al., "Tetrahedron Letters", 21:1611-1614 (1980).
Scheuer et al., Journal of the American Chemical Society 100:1, p. 307 (Jan. 4, 1978).
Graziano, et al., Chemical Abstracts 107, (1987), 236559t.
Roll et al., Org. Chem. 1988, 53 3276-8.
Negishi et al., J. Org. Chem. 45, pp. 5223-5225, (1980).
Nakagawa et al., "Aldose reductase inhibitor from Palaun sponges", Chem. Abstract 106: 96126b (1987).

*Primary Examiner*—Mukund J. Shah
*Assistant Examiner*—E. Bernhardt
*Attorney, Agent, or Firm*—Gabor L. Szekeres; Martin A. Voet; Robert J. Baran

[57] ABSTRACT

New furanone compounds have anti-inflammatory, immunosuppressive and anti-proliferative activity and are useful in treating psoriasis and modifying calcium homeostasis. A compound of the invention is 4-(1-thioacetoxytridecyl-5-hydroxy-2(5H)-furanone.

19 Claims, No Drawings

ANTI-INFLAMMATORY FURANONES

RELATED U.S. APPLICATIONS

This application is a continuation-in-part of U.S. application Ser. No. 273,294 filed Nov. 18, 1988, now abandoned.

This invention relates to new furanone compounds having anti-inflammatory activity, pharmaceutical compositions comprising these compounds and to methods of using them.

BACKGROUND OF THE INVENTION

Manoalide is a furanone compound isolated from marine sponge as reported by E.D. de Silva et al., *Tetrahedron Letters* 21:1611–1614 (1980). Anti-inflammatory, immunosuppressive and analgesic properties of manoalide are disclosed in U.S. Pat. No. 4,447,445. Manoalide has the following structural formula:

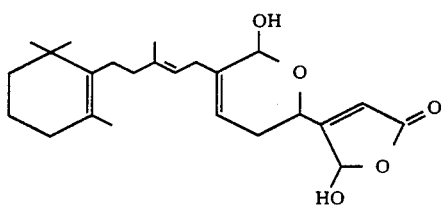

The anti-inflammatory activity of seco-manoalide and dehydro-seco-manoalide is also disclosed in U.S. Pat. No. 4,447,445.

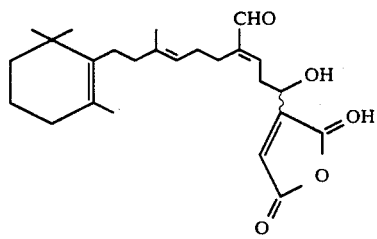

seco-manoalide

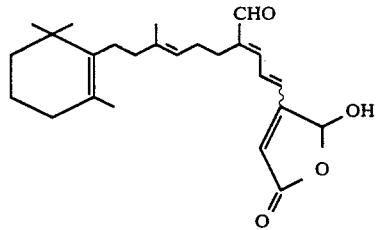

dehydro-seco-manoalide

SUMMARY OF THE INVENTION

The compounds of the present invention are represented by the following formula:

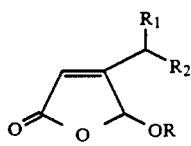

FORMULA I in which:

R is hydrogen, $C_1$–$C_6$ alkanoyl, $C_1$–$C_6$ carbamoyl, phenyl carbamoyl, $C_1$–$C_6$ dialkylphosphonate or O $$—P(OH)_2;$$

$R_1$ is halo, $NHCOR_3$, $NHSO_2R_8$, $OCOR_4$, $OR_5$ or $S(O)_mR_8$;

$R_2$ is $C_8$–$C_{20}$ alkyl;

$R_3$ is $C_1$–$C_4$ alkyl, $C_1$–$C_4$ alkoxy, trifluoromethyl, $NHR_8$ or $N$ $R_9R_{10}$;

$R_4$ is $C_1$–$C_4$ alkoxy, phenoxy or $R_6$–($C_1$–$C_4$ alkylene);

$R_5$ is $C_8$–$C_{20}$ alkyl, phenyl, 2-methoxyethyl, 2-(methoxy)ethoxymethyl, t-butyl dimethylsilyl, $PN(OR_7)R_8$, $PO(OR_7)R_8$ or $PS(OR_7)R_8$;

$R_6$ is carboxy, $C_1$–$C_4$ alkoxycarbonyl, halo or $CON$ $R_{11}R_{11}$;

$R_7$ is hydrogen or $C_1$–$C_4$ alkyl or phenyl;

$R_8$ is $C_1$–$C_4$ alkyl, hydroxy, hydrogen or $C_1$–$C_6$ alkanoyl;

$R_9$ is H or $C_1$–$C_4$ alkyl;

$R_{10}$ is H, $C_1$–$C_4$ alkyl or $SO_2NR_2R_2$;

$R_{11}$ is H or $C_1$–$C_4$ alkyl; and m is 0–2:

The hydroxy group in the 5-position on the furanone ring may be alkylated by standard procedures, for example, by reacting the hydroxyfuranone with an alkyl halide to give compounds also having anti-inflammatory activity as do the 5-hydroxyfuranones.

Particular compounds of this invention are represented by Formula I in which:

R is $C_1$–$C_6$ carbamoyl, phenylcarbamoyl, $C_1$–$C_6$ dialkyl phosphonate or $$O$$
$$—P—(OH)_2;$$

$R_3$ is $NR_9R_{10}$;

$R_5$ is $PN(OR_7)R_8$;

$R_6$ is $CONR_{11}R_{11}$; and $R_8$ is hydrogen or $C_1$–$C_6$ alkanoyl.

Specific compounds of this invention are:
4-[1-thioacetoxytridecyl-5-hydroxy-2(5H)-furanone,
4-[(1-glutarylamido)tridecyl]-5-hydroxy-2(5H)-furanone,
4-[1-(N-methylcarbamoyl)-N-methyl)carbamoyl]tridecyl-5-hydroxy-2 (5H)-furanone, and
4-[(1-phenylcarbamoyl)tridecyl]-5-hydroxy-2(5H)-furanone.

Certain of the compounds of this invention contain chiral centers and accordingly, may be prepared as enantiomeric or diasteriomeric mixtures or in optically pure form. Unless otherwise specified herein, such preparations are racemates at each chiral center. However, the scope of the invention is not to be considered as limited to these forms but also to encompass the individual optical isomers of the compounds. Compounds of the invention are prepared from 4-[$R_2$-CH(OH)-2-trimethylsilyl(TMS)-furan by procedures which are illustrated below and described in more detail in the examples.

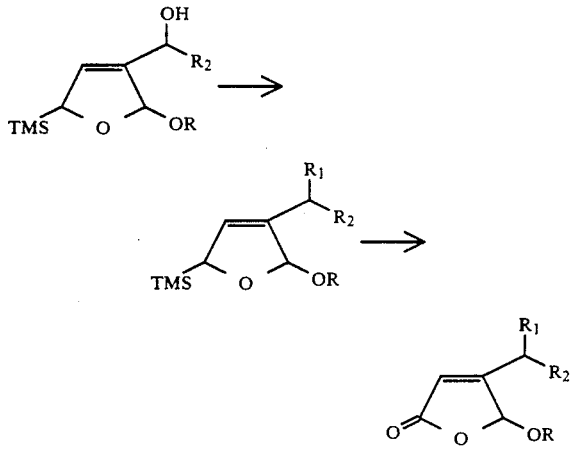

The terms $R_1$ and $R_2$ are as defined hereinabove and TMS is trimethylsilyl.

According to the above procedure, the 2-trimethylsilyl-4-($R_2$-CH(OH))-furan is reacted to convert the hydroxy group to $R_1$ and the resulting intermediate is converted to the 5-hydroxy-2-furanone by treating with oxygen and irradiating using an initiator such as Rose Bengal.

The 5-alkanoyloxy compounds (R is $C_1$–$C_4$ kanoyl) are prepared by reacting the 5-hydroxyfuranone with an acyl anhydride or halide.

The 2-trimethylsilyl-4-[$R_2$-CH(OH)]-furan starting material may be prepared by reacting 5-trimethylsilyl-3-furaldehyde with a Grignard reagent $R_2MgXhu 1$ where $X^1$ is chloro or bromo).

5-Trimethylsilyl-3-furaldehyde may be prepared by brominating 3-furaldehyde to give 5-bromo-3-furaldehyde which is converted to the dimethylacetal, then treated with t-butyl lithium and trimethylsilyl chloride.

A preferred method for preparing 5-trimethylsilyl-3-furaldehyde is by reacting lithium morpholide with 5-bromo-3-furaldehyde to protect the aldehyde group, then reacting with t-butyl lithium and trimethylsilyl chloride to give 5-trimethylsilyl-3-furaldehyde.

An improved method for preparing 5-trimethylsilyl-3-furaldehyde consists of reacting lithium morpholide with 3-furaldehyde, followed by secondary-butyl lithium, followed by trimethylsilyl chloride. This method is also advantageous for the preparation of 5-triethylsilyl-3-furaldehyde using triethylsilyl chloride. 5-Triethylsilyl-3-furaldehyde is useful as an intermediate in place of the trimethyl compound in methods described herein for preparing compounds of this invention.

In addition, this invention relates to pharmaceutical compositions containing the compounds of Formula I as active ingredients and to methods of using the compounds and pharmaceutical compositions of this invention to produce anti-inflammatory, immunosuppressant and anti-proliferative activity. These compounds are useful in treating inflammation, in suppressing unwanted immune responses and in retarding proliferation of cells. Uses include treatment of rheumatoid arthritis, osteoarthritis, rheumatic carditis and autoimmune diseases such as allergic diseases, bronchial asthma and myasthenia gravis and ocular and dermal inflammatory diseases. The compounds are useful in treating psoriasis, acne, atopic diseases and allergic conjunctivitis. They are also useful as adjuvant therapy associated with organ and tissue transplants.

The activity of the compounds of this invention is demonstrated by inhibition of the enzyme phospholipase $A_2$ in vitro and by reduction of inflammation in the mouse ear anti-inflammatory assay in vivo.

Activity of compounds of this invention may also be demonstrated by inhibition of phosphoinositide-specific phospholipase C. This activity has been reported for manoalide and may indicate anti-inflammatory utility. Bennett et al, *Molecular Pharmacology* 32:587–593 (1987).

Activity of the compounds may also be demonstrated by inhibition of ornithine decarboxylase, a rate limiting enzyme in cellular growth, which indicates use in treating psoriasis and neoplasis.

The compounds also modify calcium homeostasis. This activity is shown by effect on intracellular calcium levels in experiments using gastric glands, spleen cells, epithelial cells, $GH_3$ cells, etc. Calcium is inhibited from entering through the plasma membrane calcium channels and calcium release from intracellular stores is also blocked. Modification of calcium homeostasis is expected to have application in diseases of the nervous system involving modification of membrane lipids or transmitter release (Parkinson's, Alzheimer's), diseases of the cardiovascular system involving application of cardiac or vascular smooth muscle contractility and platelet aggregation (hypertension, cardiac infarction and atherosclerosis), diseases of the gastrointestinal tract such as ulcer disease, diarrhea, motility due to secretion of acid or $Cl^-$, diseases of the kidney involving renal handling of fluid and electrolytes (metabolic acidosis, alkalosis), and disease of abnormal growth (neoplasia, psoriasis).

The compounds of this invention have activity which is similar to that of manoalide, that is the compounds appear to be devoid of the endocrine properties of the glucocorticoids while having anti-inflammatory and immunosuppressive properties.

In the methods of this invention, the compounds of the invention are administered to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration.

Pharmaceutical compositions of this invention comprise compounds of Formula I and pharmaceutical carriers suitable for the route of administration. Standard methods for formulating pharmaceutical compositions of this type may be found in *Remington's Pharmaceutical Sciences*, Mack Publishing Company, Easton, Pa.

For topical administration, the pharmaceutical composition may be in the form of a salve, cream, ointment, spray, powder or the like. Standard pharmaceutical carriers for such compositions may be used. Preferably, compositions for topical administration will contain 0.05–5% of the active ingredient.

A typical cream formulation may contain the following:

| Ingredient | Parts by Weight |
| --- | --- |
| Water/glycol mixture (15% or more glycol) | 50-99 |
| Fatty alcohol | 1-20 |
| Non-ionic surfactant | 0-10 |
| Mineral oil | 0-10 |
| Typical pharmaceutical adjuvants | 0-5 |
| Active ingredient | 0.05-5 |

A typical ointment formulation may contain the following:

| Ingredients | Parts by Weight |
| --- | --- |
| White petrolatum | 40-94 |
| Mineral oil | 5-20 |
| Glycol solvent | 1-15 |
| Surfactant | 0-10 |
| Stabilizer | 0-10 |
| Active ingredient | 0.05-5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
| --- | --- |
| Lactose, spray-dried | 40-99 |
| Magnesium stearate | 1-2 |
| Cornstarch | 10-20 |
| Active ingredient | 0.001-20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The following examples are intended to illustrate the invention but are not limiting. All temperatures are in degrees Centigrade. NMR data are recorded in delta ppm.

Preparation of Intermediate

5-Trimethylsilyl-3-furaldehyde n-Butyl lithium (a 1.6 M solution in hexane; 31.0 ml, 49.7 mmol) was added dropwise to a solution of morpholine (4.33 ml, 49.7 mmol; freshly distilled from barium oxide) in tetrahydrofuran at $-78°$ under argon. After 15 minutes, a solution of 5-bromo-3-furaldehyde (7.5 g, 49.7 mmol) in tetrahydrofuran was added dropwise. Stirring was continued for 30 min. and n-butyl lithium (a 1.6 M solution in hexane; 46.6 ml, 74.5 mmol) was added dropwise. After 1 hour at $-78°$, chlorotrimethylsilane (18.9 ml, 149 mmol) was added and stirring continued while the cooling bath attained room temperature. The reaction mixture was quenched with 10% hydrochloric acid and the phases were separated. The aqueous phase was stirred, in the presence of ethyl ether (30 ml), with 10% hydrochloric acid at 0° C. for ½ hour. The organic phases were combined, washed (brine), dried (magnesium sulfate) and evaporated down. The residue was distilled under vacuum to give the title aldehyde as a colorless oil b.p. 48°-50° /0.25 torr.

$^1$H NMR(CDCl$_3$): 0.29(5.9H), 6.98(5.1H), 8.25(5.14) and 9.95 (5.1H).

$^{13}$C NMR (CDCl$_3$): $-2.0$, 116.2, 128.9, 155.3, 164.1 and 184.5.

MS m/e Exact mass calculated for $C_8H_{12}O_2Si$: 168.0607, found 168.0588.

Alternative Preparation of Intermediate n-Butyl lithium (a 2.5 M solution in hexane; 28.8 ml, 72 mmol) was added to a solution of morpholine (6.28 ml, 72 mmol) in tetrahydrofuran (700 ml) at $-78°$ under argon. After 20 minutes, 3-furaldehyde (7.0 g, 72 mmol) was added. After another 20 minutes, sec-butyl lithium (a 1.3 M solution in cyclohexane; 55.4 ml, 72 mmol) was added dropwise and stirring continued at $-78°$ for 7 hours before trimethylsilyl chloride (27 ml, 21.6 mmol) was added. Stirring was continued overnight (14 hours) while the cooling bath was allowed to attain room temperature. The solution was poured into ice cold 10% (v/v) hydrochloric acid (200 ml) and after stirring at 0° for 10 minutes, the layers were separated. The aqueous phase was extracted with diethyl ether. All the organic phases were combined, dried (magnesium sulfate) and evaporated down to give a light brown oil, which was purified by flash chromatography on silica using 2% ethyl ether/hexane. Fractions with R$_f$ of about 0.30 (silica, 10% ethyl ether/hexane) on evaporation gave the title aldehyde as a light yellow oil, b.p. 48-50° /0.25 torr.

$^1$H NMR(CDCl$_3$): 0.29 (s, 9H), 6.98 (s, 1H) 8.25 (s, 1H) and 9.95 (s, 1H).

$^{13}$C NMR (CDCl$_3$): $-2.0$, 116.2, 128.9, 155.3, 164.1 and 184.5.

EXAMPLE 1

3-(1-Hydroxytridecyl)-5-trimethylsilylfuran

A mixture of 1-bromododecane (2.97 g, 11.9 mmol) and magnesium turnings (300 mg, 12.5 mmol) in tetrahydrofuran (20 ml) was refluxed under argon for 30 minutes. On cooling, a solution of 5-trimethylsilyl-3-furaldehyde (1g, 5.9 mmol) in tetrahydrofuran (THF) (2 ml) was added. After 30 min., the reaction mixture was quenched with saturated ammonium chloride. Extraction (ethyl ether), drying (magnesium sulfate) and evaporation afforded an oil, which was purified by flash chromatography on silica using 15% ethyl ether/hexane. Fractions with R$_f$ of about 0.25 on evaporation gave the title alcohol as a pale yellow oil, which solified into a colorless solid on storage at $-20°$.

$^1$H NMR (CDCl$_3$): 0.26 (s, 9H), 0.91 (t, 3H, J=6.7 Hz), 1.29 (brs, 20H), 1.64 (br, 1H), 1.77 (m, 2H), 4.67 (t, 1H, J=6.8 Hz), 6.65 (s, 1H) and 7.59 (s, 1H).

MS m/e (% abundance): 339 (M$^+$+1, 9) 338 (M$^+$,31), 170 (35), 169 (100), 75 (15) and 73 (50).

4-(1-Glutaryloxytridecyl)-2-trimethylsilylfuran

Potassium bis(trimethylsilyl)amide (a 0.5 M solution in toluene; 2.23 ml, 1.12 mmol) was added dropwise to a solution of 4-(1-hydroxytridecyl)-2-trimethylsilylfuran (359 mg, 1.06 mmol) in tetrahydrofuran (6 ml) at 0° under argon. After 20 minutes, a solution of glutaric anhydride (303 mg, 2.66 mmol) in tetrahydrofuran (2 ml) was added. Stirring was continued overnight (16 hours) while the cooling bath attained room temperature. The mixture was diluted with ethyl acetate (ca. 15 ml) and quenched with brine-dilute hydrochloric acid. Extraction (ethyl acetate) and evaporation of the dried extracts (magnesium sulphate) afforded an oil, which was flash chromatographed on silica using 40% ethyl acetate/petroleum ether. The desired hemi-ester was obtained as a pale yellow oil.

$^1$H NMR (CDCl$_3$): 0.28 (s, 9H), 0.91 (t, 3H, J=7.0 Hz), 1.28 (brs, 20H), 1.85 (m, 2H), 1.98 (p, 2H, J=7.6 Hz), 2.43 (m, 4H), 5.81 (t, 1H, J=6.6 Hz), 6.61 (s, 1H), and 7.62 (s, 1H).

MS m/e (% abundance): 452 (M$^+$, 9), 338 (43), 321 (100), 249 (12), 170 (23) and 73 (53).

4-(1-Glutaryloxytridecyl)-5-hydroxy-2(5H)-furanone

A mixture of 4-(1-glutaryloxytridecyl)-2-trimethylsilylfuran (302 mg, 0.67 mmol) and Rose Bengal (5 mg) in tetrahydrofuran (7 ml) was exposed to singlet oxygen for 4 hours at −78°. The residue, after solvent removal, was flash chromatographed on silica using 40% ethyl acetate/petroleum ether. The product thus obtained was repurified using preparative TLC (two 20×20 cm, 1000μ silica plates; developed with 80% ethyl ether/petroleum ether and 5 drops of acetic acid). The title hemi-ester was obtained as a pale yellow oil, which solidified into an off-white solid at −20°.

$^1$H NMR (CDCl$_3$): 0.89 (t, 3H, J=6.8 Hz), 1.27 (brs, 20H), 1.83 (m, 2H), 1.98 (m, 2H), 2.50 (m, 4H), 5.57 (t, 1H), 5.86 (br, 2H), 6.01 (brs, 1H) and 6.11 (br, 1H).

$^{13}$C NMR (CDCl$_3$): 14.1, 19.8. 22.7, 22.9. 25.0, 25.3, 29.2, 29.4, 29.5, 29.6, 31.9, 32.1, 32.8, 33.0, 33.1, 69.6, 98.2, 118.9, 166.7, 170.3, 172.9 and 177.8.

MS m/e: Exact mass calculated for C$_{22}$H$_{40}$NO$_7$ (M+NH$_4$)$^+$430.2805, found 430.2781.

EXAMPLE 2

4-[1-(4-Carbomethoxybutanoyloxy)tridecyl]-2-trimethylsilylfuran

Methyl 4-(chloroformyl)butyrate (29 μl, 0.34 mmol) was added to a solution of 4-(1-hydroxytridecyl)-2-trimethyl silylfuran (103.5 mg, 0.31 mmol) and 4-dimethylaminopyridine (41 mg, 0.34 mmol) in tetrahydrofuran (3 ml) at room temperature. After 20 hours, the mixture was diluted with dichloromethane and quenched with water. Extraction (dichloromethane) and evaporation of the dried (magnesium sulphate) extracts gave an oil, which was purified by preparative TLC (20×20 cm, 500μ silica plate; developed with 10% ethyl ether/petroleum ether). The desired ester was obtained as a pale yellow oil.

$^1$H NMR (CDCl$_3$): 0.27 (s, 9H), 0.90 (t, 3H, J=6.7 Hz), 1.27 (brs, 20H), 1.88 (m, 2H), 1.96 (p, 2H, J=7.6 Hz), 2.39 (m, 4H), 3.69 (s, 3H), 5.79 (t, 1H, J=5.9 Hz), 6.59 (s, 1H) and 7.60 (s, 1H).

4-[1-(4-Carbomethoxybutanoyloxy)tridecyl]-5-hydroxy-2(5H)-furanone

A mixture of 4-[1-(4-carbomethoxybutanoyloxy)tridecyl]-2-trimethylsilylfuran (50 mg, 0.11 mmol) and Rose Bengal (5 mg) in tetrahydrofuran (5 ml) was exposed to singlet oxygen for 100 minutes at −78°. The residue, after solvent removal, was purified by preparative TLC (20×20 cm, 500μ silica plate; developed with 60% ethyl ether/petroleum ether). The title ester was obtained as a colorless oil.

$^1$H NMR (CDCl$_3$): 0.92 (t, 3H, J=6.8 Hz), 1.30 (brs, 20H), 1.85 (brm, 2H), 2.00 (p, 2H, J=7.4 Hz), 2.44 (t, 2H, J=7.2 Hz), 2.50 (t, 2H, J=7.2 Hz), 3.73 (s, 3H), 5.30 (br, 1H), 5.50 (brt, 1H), 5.55 (brt, 1H), 6.04 (brs, 1H), 6.06 (brs, 1H) and 6.25 (brs,1H).

$^{13}$C NMR (CDCl$_3$): 14.1, 19.9, 22.7, 25.0, 28.9, 29.0, 29.1, 29.2, 29.3, 29.5, 29.6, 30.2, 31.9, 32.6, 32.7, 32.9, 33.1, 33.2, 33.5, 51.8, 69.2, 69.8, 98.0, 98.1, 118.6, 119.4, 166.2, 167.0, 169.9, 172.4, 173.0 and 173.5.

MS m/e: Exact mass calculated for C$_{23}$H$_{42}$NO$_7$ (M+NH$_4$)$^+$444.2961, found 444.2950.

EXAMPLE 3

4-[1-(2-Methoxyethoxy)methoxytridecyl]-2-trimethylsilylfuran

A mixture of 1-bromododecane (222 mg, 0.89 mmol) and magnesium turnings (22 mg, 0.94 mmol) in tetrahydrofuran (5 ml) was refluxed under argon for 1 hour. After cooling to 0°, a solution of 5-trimethylsilyl-3-furaldehyde (150 mg, 0.89 mol) in tetrahydrofuran (1 ml) was added and conditions maintained for 1 hour. 2-Methoxyethoxymethyl chloride (0.15 ml, 1.34 mmol) was added and stirring was contained at room temperature for 16 hours. The mixture was quenched with water and extracted with ethyl ether. Evaporating of the dried (magnesium sulphate) extracts gave an oil, which was purified by preparative TLC (20×20 cm, 1000μ silica plate; developed with 15% ethyl ether/petroleum ether). The little trimethylsilylfuran was obtained as a pale yellow oil.

$^1$H NMR (CDCl$_3$): 0.28 (s, 9H), 0.91 (t, 3H, J=6.8 Hz), 1.28 (brs. 20H), 1.75 (m, 1H), 1.85 (m, 1H), 3.43 (s, 3H), 3.55 (m, 2H), 3.65 (m, 1H), 3.85 (m, 1H), 4.61 (t, 1H, J=7.3 Hz), 4.68 (dd, 2H), 6.60 (s, 1H) and 7.58 (s, 1H).

MS m/e (% abundance): 426 (M$^+$, 3), 322 (35), 321 (100), 249 (6), 154 (9) and 89 (16).

4-[-((2-Methoxyethoxy)methoxytridecyl]-5-hydroxy-2(5H)-furanone

A mixture of 4-[1-(2-methoxyethoxy)methoxytridecyl]-2-trimethylsilylfuran (150 mg, 0.35 mmol) and Rose Bengal (5 mg) in tetrahydrofuran (10 ml) was exposed to singlet oxygen for 2 hours at −78°. The residue, after solvent removal, was purified by preparative TLC (20×20 cm, 500μ silica plate; developed with 70% ethyl ether/petroleum ether). The title furanone was obtained as a pale yellow oil.

$^1$H NMR (CDCl$_3$): 0.91 (t, 3H, J=6.4 Hz), 1.29 (s, 20H), 1.75 (brm, 2H), 3.37 (s, 3H), 3.40 (m, 2H), 3.66 (m, 2H), 3.85 (m, 1H), 4.28 (m, 1H), 4.80 (dd, 2H), 5.60 (br. 1H), 5.90 (brs, 1H) and 6.10 (brs, 1H).

$^{13}$C NMR (CDCl$_3$): 14.0, 22.6, 25.2, 28.6, 28.7, 28.8, 28.9, 29.1, 29.3, 29.4, 29.6, 31.8, 35.5, 58.7, 66.8, 71.3, 73.5, 96.1, 98.1, 98.8, 118.1 and 170.3.

MS m/e: Exact mass calculated for $C_{21}H_{42}NO_6$ $(M+NH_4)^+$ 404.3012, found 404.2997.

EXAMPLE 4

4-[1-(ethoxycarbonyloxy)tridecyl]-2-trimethylsilylfuran

A mixture of 1-bromododecane (81 mg, 0.33 mmole) and magnesium turnings (8 mg, 0.33 mmole in THF (1.0 ml) was refluxed under nitrogen for 30 minutes. After cooling to 0°, a solution of 5-trimethylsilyl-3-furaldehyde (50 mg, 0.30 nmole) in tetrahydrofuran (0.5 ml) was added. The solution was stirred for one hour while the cooling bath warmed to room temperature.

Ethylchloroformate (64 mg, 0.59 mmole) was added and the solution stirred at room temperature until no starting material remained (as monitored by TLC). The mixture was quenched with water and the organic phase was dried over magnesium sulfate, filtered and concentrated. The residue was purified by preparative TLC (20×20 cm, 500 μ silica plate; developed with 5% ethyl ether/hexane). The titled compound was obtained as a colorless oil.

$^1$H NMR (CDCl$_3$): 7.64 (s, 1H), 6.62 (s, 1H), 5.6 (t, J=7.5 Hz, 1H), 4.16 (m, 2H), 1.9 (m, 1H), 1.8 (m, 1H), 1.26 (m, 23H), 0.85 (t, J=7.5 Hz, 3H), 0.225 (s, 9H).

4-[1-(Ethoxycarbonyloxy)tridecyl]-5-hydroxy-2(5H)-furanone

A mixture of 4-[1-ethoxycarbonyloxy)tridecyl]-2-trimethylsilylfuran (43.3 mg, 0.10 mmole) and Rose Bengal (5 mg) in THF (5 ml) was exposed to singlet oxygen at −78° for four hours. The residue, after solvent removal, was purified by preparative TLC (20×20 cm, 250 μ silica plate; developed with 60% ethyl ether/hexane). The title furanone was obtained as a white solid.

$^1$H NMR (CDCl$_3$): 6.25 (s, 1H), 6.08 (s, 1H), 6.02 (s, 1H), 5.35 (m, 2H), 4.2 (m, 2H), 1.84 (m, 2H) 1.35 (m, 23H), 0.85 (t, J=7.5, 3H).

$^{13}$C NMR (CDCl$_3$): 170, 169.6 166.6, 165.9, 155, 154.9, 119.4, 118.7, 97.9, 97.7, 76.5. 72.9, 72.8, 65, 64.7, 33.3, 33.1, 31.9, 29.5, 29.4, 29.3, 29.1, 24.9, 24.8, 22.6, 14.0.

MS m/e: Exact mass calculated for $C_{17}H_{28}O_3$ 280.2038 (M+), found 280.2046.

EXAMPLE 5

3-(1-Chlorotridecyl)-5-trimethylsilylfuran

Triethylamine (0.55 ml, 3.95 mmol), followed by oxalyl chloride (0.34 ml, 3.95 mmol) was added dropwise to a solution of 3-(1-hydroxytridecyl)-5-trimethylsilylfuran (890 mg, 2.63 mmol) in anhydrous dichloromethane (10 ml) at 0°. After 40 min, the reaction was quenched with ice water. Extraction (dichloromethane) and evaporation of the dried (magnesium sulfate) extracts gave an oil, which was purified by flash chromatography on silica using 5% ethyl ether/hexane. Fractions with R$_f$ of about 0.37 on evaporation gave the title chloride as a pale yellow oil, solidified to a colorless solid on storage at −20°.

$^1$H NMR (CDCl$_3$): 0.26 (s, 9H), 0.89 (t, 3H, J=6.3 Hz), 1.26 (brs, 20H), 1.85-2.05 (2m, 2H), 5.87 (t, 1H, J=7.5 Hz), 6.63 (d, 1H, J=2.3 Hz) and 7.66 (d, 1H, J=2.4 Hz)

MS m/e (% abundance): 321 (M+-Cl, 57), 180 (14), 154 (43), 153 (16), 75 (13) and 73 (100).

EXAMPLE 6

3-(1-Azidotridecyl)-5-trimethylsilylfuran

A mixture of 3-(1-chlorotridecyl)-5-trimethylsilylfuran (468 mg, 1.31 mmol) and sodium azide (852 mg, 13.1 mmol) in dry dimethylformamide (2 ml) was stirred at 60° for 6 days. Most of the solvent was evaporated under high vacuum and the residue dissolved in water. Extraction (ethyl ether) and evaporation of the dried (magnesium sulfate) extracts gave an oil, which was flash chromatographed on silica using 5% ethyl ether/hexane. Fractions with R$_f$ of about 0.73 on evaporation gave the title azide as a very pale yellow oil.

IR neat): 2100 (br, s), 1080

$^1$H NMR (CDCl$_3$): 0.26 (s, 9H), 0.88 (t, 3H, J=6.3 Hz), 1.25 (brs, 20H), 1.75 (m, 2H), 4.33 (t, 1H, J=7.3 Hz), 6.58 (s, 1H) and 7.59 (s 1H).

MS m/e: Exact mass calculated for $C_{20}H_{37}N_3O_5$ 363.2705, found 363.2698.

3-(1-Aminotridecyl)-5-trimethylsilylfuran

Lithium aluminium hydride (a 1M solution in tetrahydrofuran; 1.1 ml, 1.1 mmol) was added dropwise to a solution of 3-(1-azidotridecyl)-5-trimethylsilylfuran (334 mg, 0.92 mmol) in tetrahydrofuran at room temperature. After one hour at room temperature, the excess hydride was destroyed by adding acetone slowly to the mixture with cooling. Sodium sulfate (ca. 0.5 g) was added and the mixture was extracted thoroughly with ethyl acetate. Evaporation of the dried (magnesium sulfate) extracts gave an oil, which was purified by flash chromatography on silica using 5% methanol/dichloromethane containing 0.2% triethylamine. Fractions with R$_f$ of about 0.18 on evaporation gave the title amine as a pale yellow oil.

IR (neat): 3400-3200 (br), 1080

$^1$H NMR (CDCl$_3$): 0.29 (s, 9H), 0.92 (t, 2H, J=7.0 Hz) 1.29 (brs, 20H), 1.65 (m, 2H), 1.85 (br, 2H), 3.89 (t, 1H, J=6.8 Hz), 6.64 (s, 1H) and 7.55 (s, 1H).

MS m/e: Exact mass calculated for $C_{20}H_{38}SiN$ $(M+H)^{+3}$ 336.2722, found 336.2717.

3-[1-(Acetamido)tridecyl]-5-trimethylsilylfuran

Acetic anhydride (0.1 ml) was added to a solution of 3-(1-aminotridecyl)-5-trimethylsilylfuran (89.8 mg, 0.27 mmol) and triethylamine (0.1 ml) in dichloromethane (1 ml) at room temperature. Stirring was continued overnight (14 hours) while the cooling bath attained room temperature. The residue, after solvent removal, was purified by preparative TLC (20×20 cm, 1000μ; developed with 60% ethyl ether/hexane). The title amide was obtained as a pale yellow oil.

$^1$H NMR (CDCl$_3$): 0.26 (s. 9H), 0.89 (t, 3H, J=7.0 Hz), 1.27 (brs, 20H), 1.75 (m, 2H), 2.00 (s, 3H), 4.97 (dt, 1H, J=8.8 Hz, 7.0 Hz), 5.56 (d, 1H, J=8.8 Hz), 6.55 (s,1H) and 7.53 (s, 1H).

MS m/e: Exact mass calculated for $C_{22}H_{41}NO_2Si$ 379.2906, found 379.2908.

3-[1-(Acetamido)tridecyl)]-5-hydroxy-2(5H)-furanone

A mixture of 3-[1-(acetamido)tridecyl]-5-trimethylsilylfuran (81 mg, 0.21 mmol) and Rose Bengal (5 mg) in tetrahydrofuran (5 ml) was exposed to singlet oxygen at −78° for 2 hours. The residue, after solvent removal, was purified by preparative TLC (20×20 cm. 1000μ silica plate; developed with ethyl acetate). The title furanone was obtained as colorless solid, mp 102°-3°.

$^1$H NMR (CDCl$_3$): 0.92 (t, 3H, J=7.1 Hz), 1.29 (brs, 20H), 1.75 (m, 2H), 2.07 (brs, 3H), 4.55 (m, 1H), 4.85 (m, 1H), 5.95 (brs, 1H), 6.05 (br, 1H), 6.15 (br, 1H), 6.30 (d, 1H) and 7.0 (br, 1H).

$^{13}$C NMR (CDCl$_3$): 14.1, 22.7, 22.8, 25.8, 29.1, 29.3, 29.5, 29.6, 31.9, 33.5, 47.8, 99.2, 117.9, 170.2, 170.3 and 171.3.

MS m/e: Exact mass calculated for C$_{19}$H$_{34}$NO$_4$(M+H)+ 340.2487, found 340.2476.

EXAMPLE 7

3-[1-(Trifluoroacetamido)tridecyl]-5-trimethylsilylfuran

Trifluoroacetic anhydride (0.05 ml) was added to a solution of 3-(1-aminotridecyl)-5-trimethylsilylfuran (80.7 mg, 0.24 mmol) and triethylamine (0.1 ml) in dichloromethane (1 ml) at room temperature. Stirring was continued overnight (14 hours) while the cooling bath attained room temperature. The residue, after solvent removal, was purified by preparative TLC (20×20 cm, 1000μ silica plate; developed with 10% ethyl ether/hexane). The title amide was obtained as a pale yellow oil.

$^1$H NMR (CDCl$_3$): 0.27 (s, 9H), 0.89 (t, 3H, J=7.0 Hz), 1.26 (brs, 20H). 1.85 (m, 2H), 4.98 (dt, 1H, J=8.3 Hz, 7.5 Hz), 6.25 (d, 1H, J=8.3 Hz), 6.54 (s, 1H) and 7.58 (s, 1H).

MS M/E: Exact mass calculated for C$_{22}$H$_{38}$NO$_2$SiF$_3$(M+) 433.2624. found 433.2624.

4-[1-(Trifluoroacetamide)tridecyl]-5-hydroxy-2(5H)-furanone

A mixture of 3-[1-(trifluoroacetamido)tridecyl]-5-trimethylsilylfuran (60 mg, 0.14 mmol) and Rose Bengal (5 mg) in tetrahydrofuran (5 ml) was exposed to singlet oxygen at −78° for 2 hours. The residue, after solvent removal, was purified by preparative TLC (20×20 cm, 1000μ; 60% ethyl ether/hexane). The title furanone was obtained as a colorless solid, mp 138°-9°.

$^1$H NMR (CD$_3$OD): 0.89 (t, 3H, J=7 Hz), 1.29 (brs, 20H), 1.75-1.95 (m, 2H), 4.80-4.90 (br, 3H), 6.0 (br, 1H) and 6.15 (brs, 1H).

$^{13}$C NMR (CDCl):14.4, 23.8, 26.9, 30.0. 30.4, 30.5, 30.6, 30.8, 33.1, 100.2, 100.4, 100.6, 115.6, 119.3, 119.4, 119.5, 119.7, 119.8, 119.9, 158.6, 159.1, 169.6 and 172.3.

MS. m/e: Exact mass calculated for C$_{19}$H$_{31}$NF$_3$O$_4$ (M+H) 394.2205, found 394.2195.

EXAMPLE 8

3-[1-(Methylsulfonamido)tridecyl]-5-trimethylsilylfuran

Methanesulfonyl chloride (37 μl, 0.48 mmol) was added to a solution of 3-(1-aminotridecyl)-5-trimethylsilylfuran (134.6 mg, 0.4 mmol) and triethylamine (67 μl, 0.48 mmol) in dichloromethane (2 ml) at 0°. Stirring continued overnight (14 hours) while the cooling both attained room temperature. The reaction mixture was quenched with water. Extraction (ethyl ether) and evaporation of the dried (magnesium sulfate) extracts gave an oil, which was purified by flash chromatography on silica using 10% ethyl ether/hexane. Fractions with R$_f$ of about 0.07 on evaporation gave the title sulfonamide as a pale yellow oil.

$^1$H NMR (CDCl$_3$): 0.27 (s, 9H), 0.89 (t, 3H, J=6.4 Hz), 1.26 (brs, 20H), 1.75 (m, 2H), 2.77 (s, 3H), 4.45 (dt+d, 2H), 6.56 (1H) and 7.59 (s, 1H).

MS m/e: Exact mass calculated for C$_{21}$H$_{41}$NSiSO$_3$ (M+) 415.2581, found 415.2576.

4-[1-(Methylsulfonamido)tridecyl]-5-hydroxy-2(5H)-furanone

A mixture of 3-[1-(methylsulfonamido)tridecyl]5-trimethylsilylfuran (64 mg, 0.189 mmol) and Rose Bengal (5 mg) in tetrahydrofuran (6 ml) was exposed to singlet oxygen at −78° for 2 hours. The residue, after solvent removal, was purified by preparative TLC (20×20 cm, 1000μ silica plate; developed with 70% ethyl ether/hexane. The title furanone was obtained as an off-white solid, mp 95°-6°.

$^1$H NMR(CDCL$_3$): 0.89 (t, 3H, J=7.0 Hz), 1.26 (brs, 20 H), 1.75 (m, 2H), 3.02 (s, 3H), 4.35 (m, 1H), 5.45 (brd, 1H), 5.55 (br, 1H), 6.10 (brs. 1H) and 6.22 (br, 1H).

$^{13}$C NMR (CDCl$_3$): 13.9. 22.5, 25.5, 28.9, 29.1, 29.2, 29.4, 29.9, 31.7, 41.5, 97.9, 98.0, 119.5 and 170.7.

MS m/e: Exact mass calculated for C$_{18}$H$_{34}$SNO$_5$(M+) 376.2157, found 376.2165.

EXAMPLE 9

3-(methoxycarbonylamino)tridecyl-5-trimethylsilylfuran

Methyl chloroformate (30 μl, 0.39 mmol) was added to a solution of 3-(1-aminotridecyl)-5-trimethylsilylfuran (109.2 mg, 0.32 mmol) and triethylamine (54 μl, 0.39 mmol) in dichloromethane (2 ml) at 0°. Stirring was continued overnight (14 hours) while the cooling bath attained room temperature. The residue, after solvent removal, was purified by preparative TLC (20×20 cm, 1000μ silica plate; developed with 10% ethyl ether/hexane). The title carbamate was obtained as a pale yellow oil.

$^1$H NMR (CDCl$_3$): 0.27 (s, 9H), 0.90 (t, 3H, J=7.0 Hz), 1.27 (brs. 20H). 1.75 (m, 2H), 3.70 (s, 3H), 4.70 (bt+bd, 2H) 6.54 (5.1H) and 7.53 (s, 1H).

MS m/e: Exact mass calculated for C$_{22}$H$_{41}$SiNO$_3$ 395.2855, found 395.2842.

4-(1(methoxycarbonylamino)tridecyl-5-hydroxy-2(5H)-furanone

A mixture of 3-[1-(methylcarbamoyl)tridecyl]-5-trimethylsilylfuran (42 mg, 0.11 mmol) and Rose Bengal (5 mg) in tetrahydrofuran (6 ml) was exposed to singlet oxygen at −78° for 2βhours. The residue, after solvent removal, was purified by preparative TLC (20×20 cm, 1000μ; developed with 70% ethyl ether/hexane). The title furanone was obtained as a colorless oil, which solidified on storage, mp 77°-8°.

$^1$H NMR (CDCl$_3$): 0.89 (t, 3H, J=7.0 Hz), 1.26 (brs, 20H), 1.75 (brm, 2H), 3.69 (brs. 3H), 4.50 (br, 1H), 5.35 (br, 1H), 5.99 (brs, 1H), 6.05 (br, 1H) and 6.15 (br, 1H).

$^{13}$C NMR (CDCl$_3$): 14.1, 22.7, 25.7, 28.9, 29.1, 29.3, 29.5, 29.6, 30.0, 31.9, 33.7, 48.4, 49.1, 52.8, 52.9, 98.1, 98.6, 106.1, 118.2, 118.8, 157.0, 167.8, 170.1 and 170.4.

MS m/e: Exact mass calculated for C$_{19}$H$_{34}$NO$_5$(M+H)+ 356.2436, found 356.2431.

EXAMPLE 10

4-[1-(O-tert-Butyldimethylsilyl)tridecyl)-2-trimethylsilylfuran tert-Butyl lithium (a 1.7 M solution in pentane; 0.49 ml, 0.83 mmol) was added dropwise to a solution of 4-(1-hydroxytridecyl)-2-trimethylsilylfuran (287.2 mg, 0.85 mmol) in tetrahydrofuran (5 ml) at 0° under argon. After 10 minutes, a solution of tert-butyldimethylsilyl chloride (137 mg, 0.91 mmol) in tetrahydrofuran (1 ml) was added. Stirring was contained at room temperature for 16 hours and the mixture was quenched with water. Extraction (ethyl ether) and evaporation of the dried (magnesium sulphate) extracts afforded an oil, which was purified by preparative TLC (20×20cm, 1000μ silica plate; developed with 5% ethyl ether/hexane). The title silyl ether was obtained as a pale yellow oil.

$^1$H NMR (CDCl$_3$): −0.07 (s, 3H), 0.03 (s, 3H), 0.24 (s, 9H), 0.87 (s+m, 12H), 1.25 (brs, 20H), 1.55–1.80 (m, 2H), 4.63 (t, 1H, J=5.3 Hz), 6.53 (s, 1H) and 7.45 (s, 1H).

MS m/e (% abundance): 453 (M$^+$+1, 4), 452 (M$^+$, 2), 437 (30), 395 (80), 321 (44), 283 (46), 147 (87) and 73 (100).

4-[1-(0-tert-Butyldimethylsilyl)tridecyl]-5-hydroxy-2(5H)-furanone

A mixture of 4-[1-(0-tert-butyldimethylsilyl)tridecyl]-2-trimethylsilyl-furan (170 mg, 0.38 mmol) and Rose Bengal (5 mg) in tetrahydrofuran (7 ml) was exposed to singlet oxygen at −78 for 4 hours. The residue after so<ve©t remova<Á was purified by preparative TLC 20×20 cmÁ 500μ silica plate; developed with 30% ethyl ether/petroleum ether). The title furanone was obtained as a colorless oil.

$^1$H NMR (CDCl$_3$): 0.06 (s, 3H), 0.11 (s, 3H), 0.89 (t, 3H, J=7.0 Hz), 0.94 (s, 9H), 1.27 (brs, 20H), 1.55 (m, 2H), 4.65 (brt, 1H), 6.02 (s, 1H) and 6.04 (s, 1H).

$^{13}$C NMR (CDCl$_3$): 14.2. 18.1 22.7, 24.5, 24.7, 25.7, 29.4, 29.5, 29.6, 31.9, 35.7, 36.2, 68.7. 69.1, 97.1, 97.7, 117.9, 118.8 and 172.1.

MS m/e: Exact mass calculated for C$_{23}$H$_{45}$O$_4$Si (M+H)$^+$413.3087, found 413.3083.

EXAMPLE 11

4-[1-(0-tert-Butyldimethylsilyl)tridecyl]-5-acetoxy-2(5H)-furanone

A mixture of 4-[1 -(0-tert-butyldimethylsilyl)-tridecyl]-5-hydroxy-2(5H)-furanone (70 mg, 0.17 mmol), acetic anhydride (0.5 ml) and pyridine (0.5 ml) in tetrahydrofuran (2 ml) was stirred at room temperature for 2 days. The mixture was quenched with water and extracted with dichloromethane. Washing (aqueous copper (II) sulphate) and evaporation of the dried (magnesium sulphate) extract gave an oil, which was purified by preparative TLC (20×20 cm, 500μ silica plate; developed with 30% ethyl ether/hexane). The title acetate was obtained as a yellow oil.

1H NMR (CDCl$_3$): 0.44 (s, 3H), 0.48 (s, 3H), 1.31 (t+s, 12H), 1.65 (brs, 20H), 2.0 (brm, 2H), 2.56 (s, 3H), 2.58 (s, 3H), 4.89 (t, 1H, J=5.2 Hz), 6.48 (brs, 1H) and 7.61 (brs, 1H).

$^{13}$C NMR (CDCl$_3$): 14.1. 18.0, 20.6, 20.7, 22.7, 24.5, 25.6, 29.3, 29.4, 29.5, 29.6, 31.9, 36.5, 68.5, 92.4, 118.5, 168.8, 169.5 and 170.1.

MS m/e: Exact mass calculated for C$_{25}$H$_{47}$O$_5$Si (M+H)$^+$455.3192, found 455.3188.

EXAMPLE 12

4-[1-(4-Bromobutanoyloxy)tridecyl]-2-trimethylsilylfuran tert-Butyl lithium (a 1.7 M solution in pentane; 0.25 ml, 0.43 mmol) was added dropwise to a solution of 4-(1-hydroxytridecyl)-2-trimethylsilylfuran (120.4 mg, 0.36 mmol) in tetrahydrofuran (6 ml) at 0° under argon. After 20 minutes, a solution of 4-bromobutyryl chloride (66 mg, 0.43 mmol) in tetrahydrofuran (1 ml) was added. Stirring was continued at room temperature for 16 hours and the mixture was quenched with water. Extraction (ethyl ether) and evaporation of the dried (magnesium sulphate) extracts gave an oil, which was purified by preparative TLC (20×20 cm, 500μ silica plate; developed with 10% ethyl ether/hexane). The title ester was obtained as a yellow oil.

$^1$H NMR (CDCl$_3$): 0.30 (s, 9H), 0.93 (t, 3H, J=6.9 Hz), 1.30 (brs, 20H), 1.85 (m, 2H), 2.24 (p, 2H, J=6.6 Hz), 2.54 (t, 2H, J=7.2 Hz), 3.49 (t, 2H, J=6.4 Hz), 5.82 (t. 1H, J=7.5 Hz), 6.62 (s, 1H) and 7.64 (s, 1H).

MS m/e (% abundance): 488/486 (M$^+$, 2), 406 (9), 338 (51), 320 (10), 182 (11), 169 (11), 154 (19), 143 (14), 83 (11), 73 (95) and 69 (100).

4-[1-(4-Bromobutanoyloxy)tridecyl]-5-hydroxy-2(5H)-furanone

A mixture of 4-[1-(4-bromobutanoyloxy)tridecyl]-2-trimethylfuran (80 mg, 0.17 mmol) and Rose Bengal (5 mg) in tetrahydrofuran (7 ml) was exposed to singlet oxygen at −78° for 2 hours. The residue, after solvent removal, was purified by preparative TLC (20×20 cm, 500μ silica plate; developed with 60% ethyl ether/hexane). The title furanone was obtained as a colorless oil.

$^1$H NMR (CDCl$_3$): 0.89 (t, 3H, J=6.5 Hz), 1.26 (brs. 20H), 1.75 (m, 2H), 1.85 (m, 2H), 2.19 (p, 2H, J=6.5 Hz), 2.60 (t, 2H, J=6.7 Hz), 3.48 (t, 2H, J=6.4 Hz), 5.40 (br. 1H), 5.51 (t, 1H, J=7.5 Hz), 5.99 (brs, 1H) and 6.06 (br, 1H).

$^{13}$C NMR (CDCl$_3$): 13.2, 14.4, 23.0, 25.3. 27.7, 28.7, 28.9, 29.0, 29.4, 29.6, 29.8, 29.9, 32.2. 32.4, 32.6, 33.3, 69.9, 98.4, 98.5, 118.8, 119.0, 167.1, 170.5 and 172.7.

MS m/e: Exact mass calculated f C$_{21}$H$_{39}$BrNO$_5$ (M+NH$_4$)$^+$464.2011, found 464.2010.

EXAMPLE 13

4-Iodobutyryl chloride

A mixture of-butyrolactone (3.3 g, 38.5 mmol) and iodotrimethylsilane (10.0 g, 50 mmol) was refluxed (ca. 100° C.) for 7 hours. Chloroform (15 ml), followed by thionyl chloride (3.65 ml, 50 mmol) were added and reflux was continued for another 12 hours. The mixture was then subjected to high vacuum distillation and the title acid chloride came over at 45°-7° /0.45 torr as a purple dense oil.

$^1$H NMR (CDCl$_3$): 2.19 (p, 2H, J=6.5 Hz), 3.07 (t, 2H, J=6.5 Hz), 3.25 (t, 2H, J=6.5 Hz).

4-[1-(4-Iodobutanoyloxy)tridecyl]-2-trimethylsilylfuran tert-Butyl lithium (a 1.7 M solution in pentane; 0.33 ml, 0.56 mmol) was added dropwise to a solution of 4-(1-hydroxytridecyl)-2-trimethylsilylfuran (188.1 mg, 0.56 mmol) in tetrahydrofuran (4 ml) at 0° under argon. After 15 minutes, a solution of 4-iodobutyryl chloride (129 mg, 0.56 mmol) in tetrahydrofuran (1 ml) was added. Stirring was continued overnight while the cooling bath attained room temperature. The mixture was quenched with water and extracted with ethyl ether. Evaporation of the dried (magnesium sulphate) extracts afforded an oil, which was purified by preparative TLC (20×20 cm, 1000μ silica plate; developed with 10% ethyl ether/hexane). The title ester was obtained as a colorless oil.

$^1$H NMR (CDCl$_3$): 0.25 (s, 9H), 0.88 (t, 3H, J=6.0 Hz), 1.25 (brs, 20H). 1.80 (m, 2H), 2.11 (p, 2H, J=6.8

Hz), 2.43 (t, 2H, J=6.8 Hz), 320 (t, 2H, J=6.7 Hz), 5.77 (t, 1H, J=7.4 Hz), 6.57 (s, 1H) and 7.58 (s, 1H).

MS m/e (% abundance): 534 (M+, 8), 406 (3), 322 (24), 321 (100), 154 (3) and 73 (7).

4-[1-(4-Iodobutanoyloxy)tridecyl]-5-hydroxy-2(5H)-furanone

A mixture of 4-[(1-(4-iodobutanoyloxy)tridecyl]-2-trimethylsilylfuran (105 mg, 0.19 mmol) and Rose Bengal (5 mg) in tetrahydrofuran (10 ml) was exposed to singlet oxygen at −78° for 3 hours. The residue, after solvent removal, was purified by preparative TLC (20×20 cm, 500μ silica plate; developed with 60% ethyl ether/hexane). The title furanone was obtained as a light yellow oil.

$^1$H NMR (CDCl$_3$): 0.90 (t, 3H), 1.29 (brs, 20H), 1.86 (m, 2H), 2.15 (p, 2H, J=7.5 Hz), 2.5B(t, 2H, J=7.7 Hz), 3.27 (t, 2H, J=6.7 Hz), 5.06 (brt, 1H), 6.02 (s, 1H) and 6.05 (s, 1H).

MS m/e (% abundance): 512 ((M+NH$_4$)+, 29), 384 (100), 300 (100), 282 (25) and 104 (12).

EXAMPLE 14

A mixture of 3-(1-chlorotridecyl)-5-trimethylsilylfuran, phenol and potassium methoxide in tetrahydrofuran is stirred at room temperature to give 3-(1-phenoxytridecyl)-5-trimethylsilylfuran. A mixture of this intermediate and Rose Bengal in tetrahydrofuran is exposed to oxygen by the procedure of Example 1 to give 4-(1-phenoxytridecyl)-5-hydroxy-2(5H)-furanone.

EXAMPLE 15

By the procedure of Example 14, using the methyl ether of glycol in place of phenol, 4-[1-(methoxyethoxy)tridecyl]-5-hydroxy-2(5H)-furanone is obtained.

EXAMPLE 16

Using decanol in place of phenol in the procedure of Example 14 gives 4-[1-(decyloxy)tridecyl]-5-hydroxy(5H)-furanone.

EXAMPLE 17

3-[(N-methylureido)tridecyl]-5-Trimethylsilylfuran

A solution of methylisocyanate (23μl, 0.38mmol) in dichloromethane (0.5ml) was added to a solution of 3-(1-aminotridecyl)-5-tINMETHYLSILYLFURAN (85.5MG, 0.25 mmol) and Triethylamine (53μl.0.3mmol) in dichloromethane (2ml) at room temperature. Stirring was continued for two days and the reaction mixture was quenched with water. Extraction (dichloromethane) and evaporation of the dried (magnesium sulfate) extracts gave an oil, which was purified by preparation TLC (20×20 CM, 1000μu; developed with 40% ethyl acetate/hexane) to give the titled urea a colorless oil.

$^1$H NMR (CDCl$_3$): 0.24(s,9H), 0.88(t,3H,J=7.0Hz), 1.26(s,20H), 1.70(m,2H), 2.72(d,3H,J=4.8Hz), 4.65(M,2H), 4.80(M,1H), 6.53(S,1H) and 7.49 (S,1H).

4-[-1-(n-methylureido)tridecyl-5-hydroxy-2(5H)-furanone

A mixture of 3-[1-(N-methylureido)Tridecyl]-5-Trimethylsilyfuran (53mg. 0.14mmol) and Rose Bengal (Ca.2mg) in tetrahydrofuran (5ml) was exposed to single+oxygen at o° for 1.5 hours. The residue, after solvent removal, was purified by preparative TLC (20×20CM, 1000μ; developed with 60% ethyl acetate/hexane) to give the titled furan one as a colorless oil.

$^1$H NMR (CDCl$_3$): 0.89(t,3H,J=6.8H$_z$), 1.27(brs,20H), 1.75(br.2H), 2.74(d,3H, J-4.7H$_2$), 4.45(br.1H), 5.28(br,1H), 5.65(brs.2H), 5.98(brs,1H) and 6.10(brs,1H).

$^{13}$C NMR (CDCl$_3$): 14.1, 22.7, 24.9, 25.3, 25.8, 25.9, 26.1, 27.0, 29.0, 29.3, 29.5, 29.6, 30.1, 31.3, 31.4, 31.9, 32.5, 33.8, 33.9, 34.0, 34.1, 36.9, 48.0, 48.1, 48.2, 49.0, 50.4, 78.1, 78.2, 85.3, 87.1, 99.3, 99.4, 99.5. 116.1, 117.3, 117.9, 159.0, 159.8, 169.9, 171.4 and 171.5.

EXAMPLE 18

3-1(-aminotridecyl)-5-trimethylsilylfuran is reacted with methyl methylphosphonochloridate by the procedure of Example 17 to give 3-[1-(3-PN(OCH$_3$)(CH$_3$)O-tridecyl]-5-trimethylsilylfuran. Oxidizing by the procedure of Example 1 gives 4-[1-(3-PN(OCH$_3$)(CH$_3$)O-tridecyl]-5-hydroxy-2(5H)-furanone.

EXAMPLE 19

A mixture of 3-(1-chlorotridecyl)-5-trimethylsilylfuran, methyl mercaptan and potassium methoxide in tetrahydrofuran is stirred at room temperature to give 3-(1-methylthiotridecyl)-5-trimethylsilylfuran. Oxidizing using Rose Bengal by the procedure of Example 1 gives 4-(1-methylthiotridecyl)-5-hydroxy-2(5H)-furanone.

EXAMPLE 20

Oxidizing 3-(1-methylthiotrdecyl)-5-trimethylsilylfuran (prepared as in Example 18) with hydrogen peroxide gives the methylsulfinyl intermediate which is oxidized using Rose Bengal to give 4-(1-methylsulfinyltridecyl)-5-hydroxy-2(5H)-furanone.

EXAMPLE 21

3-(1-methylsulfinyltridecyl)-5-trimethylsilylfuran is oxidized using potassium peroxymonosulfate to give 3-(1-methylsulfonyltridecyl)-5-trimethylsilylfuran. Oxidizing with singlet oxygen by the procedure of Example 1 gives 4-(1-methylsulfonyltridecyl)-5-hydroxy-2(5H)-furanone.

EXAMPLE 22

3-[1-PO(OCH$_3$)(CH$_3$)

O-tridecyl]-5-trimethylsilylfuranone

A solution of potassium bis(trimethylsilyl)amide (a 0.5M solution in toluene; 3.19 ml, 1.59 mmol) was added dropwise to a solution of 3-(1-hydroxytridecyl)-5-trimethylsilylfuran(514mg, 1.52mmol) in tetrahydrofuran (5 ml) at 0° under argon. After 1 hour, a solution of methyl methylphosphonochloridate (235 mg, 1.83 mmol) in tetrahydrofuran (0.5 ml) was added and stirring was continued at room temperature overnight. The reaction mixture was quenched with water and extracted thoroughly with ethylether. Evaporation of the dried (magnesium sulfate) extracts gave an oil, which was purified y flash chromatography on silica using 30% ethyl ether/hexane. Fractions with R$_f$of about 0.26 on evaporation gave the title ester as a pale yellow oil.

$^1$H NMR (CDCl$_3$): 0.27 (A, 9H), 0.90(t,3H, J=7.2 H$_z$), 1.25(brs, 20H), 1.44(A, 3H), 1.50 (A,3H), 1.75–1.95(M, 2M), 3.46(d,3H, J=11.4 H$_z$), 3.72 (d, 3H, J=11.1 H$_z$), 5.45 (m, 1h), 6.64(A,1H) and 7.65(brs, 1H).

$^{13}$C NMR(COCE$_3$): −1.8, 10.3. 10.5, 12.3, 12.4, 14.0, 22.5, 25.3, 25.4, 29.1, 29.2, 29.3, 29.4, 29.5, 29.8, 31.8, 36.7, 36.8, 51.3, 51.4. 51.5, 71.3, 71.4. 118.0, 118.2, 125.3, 125.4, 125.7, 144.2, 161.4 and 162.6.

MS m/e: Exact mass calculated for $C_{22}H_{43}PO_4Si$ (M+) 4302668, found 430.2671.

4[1-PO(OCH$_3$)(CH$_3$)]

0-tridecyl]-5-hydroxy-2-(5H)-furanone

A mixture of 3-[1-PO(OCH$_3$(CH$_3$)0-tridecyl]-5-trimethylsilylfuran (168 mg, 0.39 mmol) and Rose Bengal (ca. 2 mg) in tetrahydrofuran (6 ml) was exposed to singlet oxygen at 0° for 40 min. The residue, after solvent removal, was purified by preparative TLC (20×20 cm, 1000μ; developed with ethyl acetate) to give the title furanone.

$^1$H NMR(COCE$_3$): 0.91(t, 3H, J=6.9Hz), 1.29(brs, 20H), 1.54(d,3H,J=6.6Hz), 1.60(d, 3H, J=6.3Hz), 1.85(br, 2H), 3.73(d,3H, J=11.1 Hz), 3.79 (d,3H,J=11.1 Hz), 5.15(m, 1H), 6.0–6.3(m, 2H) and 7.0(br, 1H).

$^{13}$C NMR (COCE$_3$): 9.8, 9.9, 11.7, 11.9, 14.0, 22.6. 22.8, 24.4, 24.6, 28.9, 29.1, 29.3, 29.4, 29.5, 29.6, 31.8, 34.4, 34.6, 52.5, 52.6, 52.8, 52.9, 71.6, 71.7,. 71.9. 98.0, 98.1, 118.7, 167.7, 169.9 and 170.3.

MS m/e. Exact mass calculated for $C_{19}H_{36}O_6P$ (M+) 3912250, found 391.2263.

EXAMPLE 23

4-(1-Thioacetoxytridecyl)-2-Triethylsilylfuran

A mixture of bis-[1-(2-triethylsilyl-4-furyl)tridecyl]oxalate (1.95 g, 5.49 mmol) and potassium thioacetate (1.25 g, 10.9 mmol) in DMF (20 ml) was warmed at 70° C. for 2 days. After most of the solvent was removed under vacuum, the reside was dissolved in water. Extraction (ethyl ether), drying (magnesium sulfate) and evaporation of the extracts gave a residue which was purified by a silica column using 3% ethyl ether/hexane. Fractions with R$_f$ of about 0.43 on evaporation gave the titled thioester.

$^1$H NMR (CDCl$_3$): 0.78 (q, 6H, J=7.7 Hz), 0.91 (t, 3H, J=6.8 Hz), 1.00 (q, 9H, J=8.7 Hz), 1.28 (brs, 20H), 1.85 (m, 2H), 2.34 (s, 3H), 4.58 (t, 1H, J=7.5 Hz), 6.54 (brs, 1H) and 7.57 (s, 1H).

HRMS exact mass calculated for $C_{25}H_{46}SO_2S$ (M+) 438.2987, found 438.2976.

4-(1-Thioacetoxytridecyl)-5-hydroxy-2(5H)-furanone

A mixture of 4-(1-thioacetoxytridecyl)-2-triethylsilylfuran (200 mg, 0.46 mmol), water (a few drops) and Rose Bengal (5 mg) in acetone was exposed to singlet oxygen at 0° for 2 hours. The residue, after solvent removal, was purified by preparative TLC using 60% ethyl ether/hexane to give the titled furanone.

$^1$H NMR (CDCl$_3$): 0.88 (t, 3H, J=6.4 Hz), 1.25 (m, 20H), 1.73 (m, 2H), 2.39 (s, 3H), 4.20 (t. 1H, 7.5 Hz), 4.38 (t, 1H, J=7.5 Hz), 5.15 (br, 1H), 5.90 (brs, 2H), 6.03 (brs, 1H) and 6.08 (brs, 1H).

$^{13}$C NMR (CDCL$_3$): 14.0, 22.6, 26.7, 27.3, 27.6, 29.0. 29.3, 29.4, 29.6, 32.2, 39.6, 39.7, 40.4, 40.6, 98.5, 98.6, 118.6, 118.7, 119.3, 119.4, 186.4, 186.8, 170.6 and 195.0.

HRMS exact mass calculated for $C_{19}H_{33}O_4S$ (M+H)+35.7.2099, found 357.2103.

EXAMPLE 24

4-[(1-Glutarylamido)tridecyl]-2-triethylsilylfuran

A mixture of 4-(1-aminotridecyl)-2-triethylsilylfuran (250 mg, 0.66 mmol) and glutaric anhydride (150 mg, 1.32 mmol) in dichloromethane was stirred at room temperature for 2 days. The mixture was quenched with dilute hydrochloric acid and was extracted thoroughly with ethyl acetate. Evaporation of the dried (magnesium sulfate) extracts gave a residue which was purified by a silica column using 5% methanol/dichloromethane to give the titled amide as a colorless solid.

$^1$H NMR (CDCl$_3$): 0.75 (q, 6H, J=8.0 Hz), 0.88 (t, 3H, J=6.5 Hz), 0.99 (t, 9H, J=8.0 Hz), 1.24 (m, 20H), 1.70 (p, 2H, J=7.3 Hz), 1.97 (m, 2H), 2.28 (t, 2H, J=23 Hz), 2.41 (t, 2H, J=7.3 Hz), 4.97 (q, 1H, J=8.2 Hz), 5.65 (d, 1H, J=8.2 Hz), 6.50 (s, 1H) and 7.50 (s, 1H).

$^{13}$C NMR (CDCL$_3$): 3.15, 7.30, 14.1, 20.8, 22.7, 26.0, 29.3, 29.5, 29.6, 31.9, 33.0, 35.3, 35.4, 45.3, 119.7, 126.3, 143.4, 159.5, 171.5 and 177.8.

HRMS exact mass calculated for $C_{28}H_{51}NO_4Si$ (M+) 493.3587, found 493.3577.

4-[(1-Glutarylamido)tridecyl]-5-hydroxy-2(5H)-furanone

A mixture of 4-[(1-glutarylamido)tridecyl]-2-triethylsilylfuran (222.5 mg, 0.45 mmol), water (a few drops) and Rose Bengal (5 mg) was exposed to single oxygen at 0° for 1.5 hours. The residue, after solvent removal, was purified by a silica column using 10% methanol/chloroform to give the titled furanone as a colorless solid.

$^1$H NMR (CD$_3$OD): 0.79 (t, 3H, J=6.5 Hz), 1.18 (m, 20H), 1.50 (m, 2H), 1.80 (t, 2H, J=7.0 Hz), 2.23 (t, 4H, J=7.0 Hz), 4.60 (m, 1H), 4.73 (m, 1H), 5.82 (brs, 1H), 5.88 (brs, 1H), 5.99 (brs, 1H), 8.20 (m, 1H) and 8.30 (m, 1H).

$^{13}$C NMR (CD$_3$OD): 14.4, 22.2, 23.7, 26.9, 30.1, 30.5, 30.7, 30.8, 33.0, 34.0, 35.8, 99.8, 100.3, 118.1, 118.7, 172.1, 172.7, 172.8, 175.1 and 176.7.

HRMS exact mass calculated for $C_{22}H_{38}NO_6$ (M+H)+412.2696, found 412.2696.

EXAMPLE 25

4-[1-(N-(N-Methylcarbamoyl)-N-methyl)carbamoyloxy tridecyl-2-trimethylsilylfuran A mixture of methylisocyanate (60 μl, 1.05 mmol), 4-(1-hydroxytridecyl)-2-trimethylsilylfuran (355.7 mg, 1.05 mmol), copper (I) chloride (104 mg, 1.05 mmol) in DMF (5 ml) was stirred at room temperature for 2 days. After most of the solvent was evaporated, the residue was dissolved in water. Extraction (ethyl ether), drying (magnesium sulfate) and evaporation of the extracts gave a residue, which was purified by a SiO$_2$ column using 30% ethyl ether/hexane. Fractions with R$_f$ of about 0.36 on evaporation gave the titled carbamate.

$^1$H NMR (CDCl$_3$): 0.29 (s, 9H), 0.91 (t, 3H, J=6.9 Hz), 1.28 (brs, 20H), 1.90 (m, 2H), 2.87 (d, 3H, J=4.5 Hz), 3.26 (s, 3H), 5.73 (t, 1H, J=7.7 Hz), 6.60 (s, 1H), 7.64 (s, 1H) and 8.55 (br, 1H).

HRMS exact mass calculated for $C_{24}H_{44}N_2O_4Si$ 452.3070, found 452.3058.

4-[1-(N-(N-Methylcarbamoyl)-N-methyl)carbamoyloxy tridecyl-5-hydroxy-2(5H)-furanone

A mixture of 4-[1-(N-(N-methylcarbamoyl)-N-methyl) carbamoyl]tridecyl-2-trimethylsilylfuran (270 mg, 0.59 mmol), water (a few drops) and Rose Bengal (6.5 mg) in acetone was exposed to singlet oxygen at 0° for 4 hours. The residue, after solvent removal, was purified by a silica column using 80% ethyl ether/hexane to give the titled furanone as a colorless solid.

$^1$H NMR (CDCl$_3$): 0.88 (t, 3H, J=6.5 Hz), 1.26 (m, 20H), 2.90 (m, 2H), 2.85 (d, 3H, J=3.0 Hz), 2.87 (d, 3H, J=4.7 Hz), 4.75 (m, 1H), 4.90 (m, 1H), 5.43 (t, 1H, J=6.3 Hz), 5.52 (t, 1H, J=6.3 Hz), 6.03 (s, 2H). 6.05 (d, 1H, J=4.5 Hz), 6.22 (d, 1H, J=6.8 Hz), 8.27 (m, 1H) and 8.40 (m, 1H).

$^{13}$C NMR (CDCl$_3$): 13.8, 22.4, 24.6, 24.8, 27.1, 28.9, 29.1, 29.2, 29.3, 29.4, 30.7, 31.6, 32.8, 32.9, 71.8, 72.2, 97.9, 98.1, 118.7, 119.6, 155.3, 155.6, 155.7, 166.0, 166.5, 170.1 and 170.4.

HRMS exact mass calculated for C$_{21}$H$_{37}$N$_2$O$_6$ (M+H)$^+$ 413.2652, found 413.2660.

EXAMPLE 26

4-[(1-Phenylcarbamoyloxy)tridecyl]-2-trimethylsilylfuran

Tert-butyl lithium (a 1.7 M solution in pentane; 0.38 ml, 0.65 mmol) was added to a solution of 4-(1-hydroxytridecyl)-2-trimethylsilylfuran (200 mg, 0.59 mmol) in THF at 0° under argon. After 30 minutes, phenyl isocyanate (70 μl, 0.65 mmol) was added and stirring was continued overnight while the cooling bath warmed to room temperature. The mixture was quenched with water and extracted thoroughly with ethyl ether. Evaporation of the dried (magnesium sulfate) extracts gave a residue, which was purified by a silica column using 5% ethyl ether/hexane to give the titled carbamate.

$^1$H NMR (CDCl$_3$): 0.25 (s, 9H), 0.89 (t, 3H, J=6.5 Hz), 1.25 (m, 20H), 1.80 (m, 1H), 1.90 (m, 1H), 5.77 (t, 1H, J=7.3 Hz), 6.56 (br, 1H), 6.62 (s, 1H), 7.05 (t, 1H, J=7.2 Hz), 7.30 (t, 2H, J=7.3 Hz), 7.37 (d, 2H, J=8.2 Hz) and 7.64 (s, 1H).

$^{13}$C NMR (CDCl$_3$): −2.0, 13.8, 22.4, 25.3, 28.1, 29.1, 29.3, 29.4, 31.7, 34.8, 69.6, 118.6, 118.7, 123.4, 125.2, 129.1, 129.2, 138.1, 144.7, 153.3 and 161.6.

4-[(1-Phenylcarbamoyloxy)tridecyl]-5-hydroxy-2(5H)-furanone

A mixture of 4-[(1-phenylcarbamoyl)tridecyl]-2-trimethylsilylfuran (201.3 mg, 0.44 mmol), water (a few drops) and Rose Bengal (6.5 mg) in acetone was exposed to singlet oxygen at 0° for 3 hours. The residue, after solvent removal, was purified by a silica column using 70% ethyl ether/hexane. Fractions with R$_f$ of about 0.45 on evaporation gave the titled furanone.

$^1$H NMR (CDCl$_3$): 0.88 (t, 3H, J=6.6 Hz), 1.26 (m, 20H), 1.84 (m, 2H), 5.30 (brm, 2H), 6.03 (brs, 1H), 6.08 (brs, 1H), 6.79 (brm, 1H), 7.12 (m, 1H) and 7.30 (m, 4H).

$^{13}$C NMR (CDCl$_3$): 14.0, 22.6, 24.7, 24.9, 25.0, 28.6, 28.8, 28.9, 29.0, 29.1, 29.2, 29.3, 29.4, 29.6, 31.8, 32.9, 33.3, 70.0, 70.4, 98.2, 118.4, 119.0, 124.0, 129.0, 137.0, 153.1, 166.9, 167.6, 170.6 and 170.8.

EXAMPLE 27

4-(1-Diethylphosphonyl)tridecyl-2-trimethylsilylfuran

Potassium bis (trimethylsilyl) amide (a 0.5 M solution in toluene; 6.5 ml; 3.25 mmol) was added to a solution of 4-(1-hydroxytridecyl)-2-trimethylsilylfuran (1.0 g, 2.95 mmol) in tetrahydrofuran (10 ml) at 0° under argon. After 30 min, diethyl chlorophosphate (0.64 ml, 4.42 mmol) was added. Stirring was continued for 14 hours while the cooling bath attained room temperature. The mixture was quenched with water and was extracted with ethyl ether. Evaporation of the dried (magnesium sulfate) extracts gave an oil, which was purified by a silica column using 50% ethyl ether/hexane to give the titled ester.

$^1$H NMR (CDCl$_3$): 0.25 (s, 9H), 0.88 (t, 3H, J=6.5 Hz), 1.85 (t, 3H, J=6.9 Hz), 1.25 (m, 20H), 1.29 (t, 3H, J=8.2 Hz), 1.42 (t, 3H, J=8.3 Hz), 1.80 (m, 1H), 1.95 (m, 1H), 3.91 (P, 2H, J=7.3 Hz), 4.05 (m, 2H), 4.28 (m, 2H), 5.29 (dd, 1H, J=13.8 Hz, 6.9 Hz), 6.65 (s, 1H) and 7.64 (s, 1H).

$^{13}$C NMR (CDCl$_3$): −1.93, 13.9, 15.6, 15.7, 15.8, 15.9, 22.5, 25.1, 29.0, 29.2, 29.3, 29.4, 29.5, 31.7, 36.3, 36.4, 63.1, 63.2, 63.3, 73.1, 73.2, 118.2, 125.0, 125.1, 144.3 and 161.2.

4-(1-Diethylphosphonyl)tridecyl-5-hydroxy-2(5H)-furanone

A mixture of 4-(1-diethylphosphonyl)tridecyl-2-trimethylsilylfuran (100 mg, 0.22 mmol), water (a few drops) and Rose Bengal (5 mg) in acetone (10 ml) was exposed to singlet oxygen at 0° for 3 hours. The residue, after solvent removal, was purified by a silica column using 60% ethyl acetate/hexane to give the titled furanone.

$^1$H NMR (CDCl$_3$): 0.88 (t, 3H, J=6.4 Hz), 1.26 (m, 20H), 1.35 (m, 6H), 1.80 (m, 2H), 4.14 (q, 4H, J=7.6 Hz), 5.06 (brm, 1H), 5.96 (brs, 1H), 6.10 (brs, 1H), 6.16 (brs, 1H), 6.20 (brs, 1H) and 6.54 (br, 1H).

$^{13}$C NMR (CDCl$_3$): 14.0, 15.2, 15.9, 16.0, 22.6, 24.4, 29.1, 29.3, 29.4, 29.5, 29.6, 31.8, 34.4, 64.4, 64.5, 73.6, 73.7, 98.1, 119.8, 166.4 and 169.9.

EXAMPLE 28

A mixture of 4-[1-PO(OEt)$_2$]-2-triethylsilylfuran and bromotrimethyl-silane is stirred at room temperature to give 4-[1-PO(OH)$_2$]-2-triethylsilylfuran. Oxidizing using Rose Bengal and a few drops of water by the procedure of Example 1 gives 4-[1-PO(OH)$_2$]-5-hydroxy-2(5H)-furanone.

EXAMPLE 29

Using diethyl chlorothiophosphate in place of diethyl chlorophosphate in the procedure of Example 27 gives 4-[1-PS(OEt)$_2$]-5-hydroxy-2(5H)-furanone.

EXAMPLE 30

Using 4-[1-PS(OEt)$_2$]-2-triethylsilylfuran in place of 4-[1-PO(OEt)$_2$]-2-triethylsilylfuran of Example 28 gives 4-[1-PS(OH)$_2$]-5-hydroxy-2(5H)-furanone.

EXAMPLE 31

Using 4-(1-aminotridecyl)-5-triethylsilylfuran in place of 4-(1-hydroxy-tridecyl)-5-triethylsilylfuran in the procedure of Example 27 gives 4-[1-PN(OEt)$_2$]-5-hydroxy-2(5H)-furanone.

EXAMPLE 32

Using 4-[1-PN(OEt)$_2$]-2-triethylsilylfuran in place of 4-[1-PO(OEt)$_2$]-2-triethylsilylfuran of Example 28 gives 4-[1-PN(OH)$_2$]-5-hydroxy-2(5H)-furanone.

EXAMPLE 33

A mixture of 4-(1-glutaryloxytridecyl)-2- trimethylsilylfuran, oxalyl chloride and diethylamine was stirred at 0° to give 4-[1-OCO(CH$_2$)$_3$CONEt$_2$]-2-trimethylsilylfuran. Oxidizing using Rose Bengal by the procedure of Example 1 gives 4-[1-OCO(CH$_2$)$_3$CONE+$_2$]5-hydroxy-2(5H) -furanone.

EXAMPLE 34

Reacting 4-(1-hydroxytridecyl)-2-triethylsilylfuran with chlorosulfonylisocyanate followed by hydrolysis gives 4-(1-carbamoyl) tridecyl-2-triethylsilylfuran. Oxidizing using Rose Bengal by the procedure of Example 1 gives 4-(1-carbamoyl)tridecyl-5-hydroxy-2(5H)-furanone.

EXAMPLE 35

Substituting 4-(1-hydroxytridecyl)-2-triethylsilylfuran in Example 34 with 4-(1-aminotridecyl)-2-triethylsilylfuran gives 4-(1-uredo)tridecyl-5-hydroxy-2(5H)-furanone.

EXAMPLE 36

Reacting 4-(1-hydroxytridecyl)-2-triethylsilylfuran successively with chlorosulfonyl isocyanate and diethylamine gives 4-(N-(N',N''-diethylsulfonylamido)carbamoyl)tridecyl 2-triethylsilylfuran. Oxidizing this intermediate with oxygen using Rose Bengal as the indicator gives 4-(-N-(N',N''-diethylsulfonylamido)carbamoyl)tridecyl-5-hydroxy-2(5H)-furanone.

What is claimed is:

1. A compound of the formula

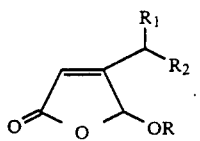

in which:

R is hydrogen, $C_1$–$C_6$alkanoyl, $C_1$–$C_6$ carbamoyl, phenyl carbamoyl, $C_1$–$C_6$ dialkylphosphonate or PO(OH)$_2$;

$R_1$ is halo,

NHCOR$_3$,

NHSO$_2$R$_8$,

NHPO(OCH$_3$)CH$_3$;

OCOR$_4$,

OR$_5$ or

S(O)$_m$R$_8$;

SCOCH$_3$;

OCONH-phenyl;

OCO-N(CH$_3$)CONH(CH$_3$)]

$R_2$ is $C_8$–$C_{20}$ alkyl;

$R_3$ is $C_1$–$C_4$ alkyl, $C_1$–$C_4$ alkyoxy, trifluoromethyl, —(CH$_2$)$_3$—COOH, NHR$_8$ or N—R$_9$R$_{10}$;

$R_4$ is $C_1$–$C_4$ alkoxy, phenoxy, R$_6$-($C_1$–$C_4$ alkyl), or NHSO$_2$N(C$_2$H$_5$)$_2$; p1 R$_5$ is $C_8$–$C_{20}$ alkyl, phenyl, 2-methoxyethyl, 2-(methoxy) ethoxymethyl, t-butyl dimethylsilyl, PO(OR$_7$)R$_8$ or PS(OR$_7$)R$_8$;

$R_6$ is carboxy, $C_1$–$C_4$ alkoxycarbonyl, halo or CONR$_{11}$R$_{11}$;

$R_7$ is hydrogen or $C_1$–$C_4$ alkyl or phenyl;

$R_8$ is $C_1$–$C_4$ alkyl, ethoxy, hydroxy, hydrogen or $C_1$–$C_6$ alkanoyl;

$R_9$ is H or $C_1$–$C_4$ alkyl;

$R_{10}$ is H, $C_1$–$C_4$ alkyl or SO$_2$NR$_2$R$_2$;

$R_{11}$ is H or $C_1$–$C_4$ alkyl; and m is 0–2.

2. A compound the formula:

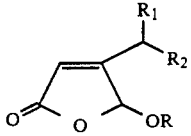

in which

R is hydrogen, $C_1$–$C_6$alkyanoyl, $C_1$–$C_6$ carbamoyl, phenyl carbamoyl, $C_1$–$C_6$ dialkylphosphonate or PO(OH)$_2$; $R_1$ is chloro, acetamido, methoxycarbonylamino, culfonamide, 4-carboxybutanoyloxy, 4-carbomethoxybutanoyloxy, 2-methoxyethoxymethoxy, ethoxycarbonyloxy, 4-bromobutanoyloxy or 4-iodobutanoyloxy, and $R_2$ is $C_8$–$C_{20}$ alkyl.

3. A compound of claim 2 in which R is hydrogen.

4. A compound of claim 2 where $R_2$ is dodecyl.

5. A compound which is 4-(1-thioacetoxytridecyl)-5-hydroxy-2(5H)-furanone.

6. A compound which is 4-[1-(glutarylamido)-tridecyl]-5-hydroxy-2(5H)-furanone.

7. A compound which is 4-[1-(N-methylcarbamoyl)-N-methyl)carbamoyl]tridecyl-5-hydroxy-2(5H)furanone.

8. A compound which is 4-[(1-phenylcarbamoyl)-tridecyl]-5-hydroxy-2(5H)-furanone.

9. A compound which is 4-[1-ethoxycarbonyloxy)-tridecyl]-5-hydroxy-2(5H)-furanone.

10. A compound which is 4-[1-(4-carboxybutanoyloxy)tridecyl]-5-hydroxy-2(5H)-furanone.

11. A compound which is 4-[1-4-carbomethoxybutanoyloxy)tridecyl]-5-hydroxy-2(5H)-furanone.

12. A compound which is 4-[1-(2-methoxyethoxy)methoxytridecyl]-5-hydroxy-2(5H)-furanone.

13. A compound which is 4-[1-(methylsulfonamido)-tridecyl]-5-hydroxy-2(5H)-furanone.

14. A compound which is 4-(1-(methoxycarbonylamino)tridecyl]-5-hydroxy-2(5H)-furanone.

15. A compound which is 4-[1-(4-bromobutanoyloxy)tridecyl]-5-hydroxy-2(5H)-furanone.

16. A compound which is 4-[1-PO(OCH$_3$)CH$_3$O-tridecyl]-5-hydroxy-2(5H)-furanone.

17. A pharmaceutical composition which comprises a pharmaceutical carrier and a therapeutically effective amount of a compound of claim 1.

18. A method of treating inflammation or an allergic response in a mammal which comprises administering to a mammal a therapeutically effective amount of a compound of claim 1 above or in conjunction with a pharmaceutically acceptable excipient.

19. A method of treating psoriasis which comprises administering to a mammal a therapeutically effective amount of a compound of claim 1 either above or in conjunction with a pharmaceutically acceptable excipient.

* * * * *

UNITED STATES PATENT AND TRADEMARK OFFICE
CERTIFICATE OF CORRECTION

PATENT NO. : 5,089,485
DATED : February 18, 1992
INVENTOR(S) : Gary C. M. Lee

It is certified that error appears in the above-indentified patent and that said Letters Patent is hereby corrected as shown below:

Column 3, line 34, "kanoyl" should be —alkanoyl—;

Column 3, line 39, before "$R_2MgXhu$" insert —(—;

Column 5, line 45, after "subcutaneous" change "." to —,—;

Column 8, line 64, change "(br." to —(br,—;

Column 9, line 11, "nmole" should be —mmole—;

Column 11, line 44, "(CDCl)" should be —$(CDCl_3)$—;

Column 13, line 22, "-78" should be — $-78°$ —;

Column 13, line 24, after "TLC" insert —AE—;

Column 13, line 39, after "4-[1" there should be no space;

Column 15, line 41, "hydroxy(5H)" should be —hydroxy-2(5H)—;

Column 15, line 61, after "tridecyl" insert —]—;

Column 16, line 31, "methylthiotrdecyl" should be —methylthiotridecyl—;

Column 17, line 23, "m/e." should be —m/e:—;

Column 17, line 54, "(t." should be —(t,—;

Column 17, line 57, "29.0." should be —29.0,—;

UNITED STATES PATENT AND TRADEMARK OFFICE
CERTIFICATE OF CORRECTION

PATENT NO. : 5,089,485
DATED : February 18, 1992
INVENTOR(S) : Gary C. M. Lee

It is certified that error appears in the above-indentified patent and that said Letters Patent is hereby corrected as shown below:

Column 18, line 21, "single" should be —singlet—;
Column 18, line 33, after "172.1," insert —172.6,—;
Column 21, line 52, the "1" after ")" (second occurrence) should be —;—;
Column 21, line 56, "alkyoxy," should be —alkoxy,—;
Column 21, line 59, delete "p1", then start "$R_5$" with a new paragraph;
Column 22, line 7, after "compound" insert —of—;
Column 22, line 16, insert a space after "$C_6$"; and Signed and Sealed this Nineteenth Day of July, 1994

Attest:

BRUCE LEHMAN

*Attesting Officer*   *Commissioner of Patents and Trademarks*